United States Patent
Zeiher et al.

(10) Patent No.: US 7,919,315 B2
(45) Date of Patent: Apr. 5, 2011

(54) IN VITRO METHOD FOR THE DIAGNOSIS OF CARDIOVASCULAR FUNCTIONALITY OF BONE MARROW PRECURSOR CELLS (BMPS) AND/OR BLOOD-DERIVED CIRCULATING PRECURSOR CELLS (BDPS)

(75) Inventors: Andreas M. Zeiher, Frankfurt (DE); Christopher Heeschen, Munich (DE); Stefanie Dimmeler, Frankfurt (DE)

(73) Assignee: T2Cure GmbH (DE)

( * ) Notice: Subject to any disclaimer, the term of this patent is extended or adjusted under 35 U.S.C. 154(b) by 940 days.

(21) Appl. No.: 10/574,380

(22) PCT Filed: Oct. 13, 2004

(86) PCT No.: PCT/EP2004/011503
§ 371 (c)(1),
(2), (4) Date: Mar. 9, 2007

(87) PCT Pub. No.: WO2005/038454
PCT Pub. Date: Apr. 28, 2005

(65) Prior Publication Data
US 2007/0274959 A1      Nov. 29, 2007

(30) Foreign Application Priority Data
Oct. 13, 2003   (DE) ................................ 103 47 436

(51) Int. Cl.
*C12N 5/08*   (2006.01)
(52) U.S. Cl. ........................................ 435/372; 435/374
(58) Field of Classification Search .................... None
See application file for complete search history.

(56) References Cited

OTHER PUBLICATIONS

Vasa, M. et al., Number and migratory activity of circulating endothelial progenitor cells inversely correlate with risk factors for coronary artery disease, *Circulation Research* 89(1): E1-E7, 2001.
Yamaguchi, J.-I. et al., Stromal cell-derived factor-1 effects on ex vivo expanded endothelial progenitor cell recruitment for ischemic neovascularization, *Circulation* 107(9) 1322-1328, 2003.
Assmus, B. et al., Transplantation of progenitor cells and regeneration enhancement in acute myocardial infarction (TOPCARE-AMI), *Circulation* 106(24) 3009-3017, 2002.
Kim, C.H. et al., In vitro behavior of hematopoietic progenitor cells under the influence of chemoattractants: stromal cell-derived Factor-1, steel factor, and the bone marrow environment, Blood 91(1), 100-110, 1998.

*Primary Examiner* — Michail A Belyavskyi
(74) *Attorney, Agent, or Firm* — Barry L. Davison; David Wright Tremaine LLP (57) ABSTRACT

The present invention relates to an in vitro method for the analysis of a sample from a mammal in connection with cardiovascular diseases, wherein the method comprises the following steps: a) isolating of bone marrow-precursor cells (BMPs) and/or blood-derived circulating precursor cells (BDPs) by means of cell specific surface markers, and b) detecting the cardiovascular functionality of the isolated BMPs and/or BDPs by means of a suitable migration assay. The method according to the invention can be employed as a kit in the context of the diagnosis and/or the prognosis of cardiovascular diseases, for the monitoring of their therapies and/or for a stratification for a prospective cell therapy with stem- and/or precursor cells in order to increase the perfusion of ischemic tissue or for a regeneration of tissue losses (e.g. heart insufficiency), respectively. In a further aspect, the present invention then relates to an in vitro method for isolating specific bone marrow-precursor cells by means of a suitable migration assay. According to the invention, these BMPs and/or BDPs can be used for the treatment of cardiovascular diseases, selected from the group consisting of stable coronary heart disease, acute coronary syndrome, acute myocardial infarction, chronic ischemic cardiomyopathy (ICMP), dilatative cardiomyopathy (DCM) or other causes for a heart insufficiency.

20 Claims, 7 Drawing Sheets

Figure 1A: Quantitative LV-angiography – global ejection fraction

Figure 2: Correlation between baseline ejection fraction and functional improvement Figure 3: Migratory capacity and differences in the regional wall movement and risk of infarction

IN VITRO METHOD FOR THE DIAGNOSIS OF CARDIOVASCULAR FUNCTIONALITY OF BONE MARROW PRECURSOR CELLS (BMPS) AND/OR BLOOD-DERIVED CIRCULATING PRECURSOR CELLS (BDPS)

This application is a National Stage Application of International Application Number PCT/EP2004/011503, filed Oct. 13, 2004; which claims priority to German Application No. 10347 436.6, filed Oct. 13, 2003.

The present invention relates to an in vitro method for the analysis of a sample from a mammal in connection with cardiovascular diseases, wherein the method comprises the following steps: a) isolating of bone marrow-precursor cells (BMPs) and/or blood-derived circulating precursor cells (BDPs) by means of cell specific surface markers, and b) detecting the cardiovascular functionality of the isolated BMPs and/or BDPs by means of a suitable migration assay. The method according to the invention can be employed as a kit in the context of the diagnosis and/or the prognosis of cardiovascular diseases, for the monitoring of their therapies and/or for a stratification for a prospective cell therapy with stem- and/or precursor cells in order to increase the perfusion of ischemic tissue or for a regeneration of tissue losses (e.g. heart insufficiency), respectively. In a further aspect, the present invention then relates to an in vitro method for isolating specific bone marrow-precursor cells (BMPs) and/or blood-derived circulating precursor cells (BDPs), comprising: a) taking a sample from a mammalian donor, b) isolating of BMPs and/or BDPs by means of cell specific surface markers from the sample so obtained, and c) detecting the cardiovascular functionality of the isolated BMP and/or BDP by means of a suitable migration assay. According to the invention, these BMPs and/or BDPs can be used for the treatment of cardiovascular diseases, selected from the group consisting of stable coronary heart disease, acute coronary syndrome, acute myocardial infarction, chronic ischemic cardiomyopathy (ICMP), dilatative cardiomyopathy (DCM) or other causes for a heart insufficiency, and can be inter alia present in a pharmaceutical composition.

Post-infarction heart failure remains a major cause of morbidity and mortality. Although an immediate reperfusion of the occluded artery leads to significantly reduced mortality rates (Lange R A, Hillis L D. Reperfusion therapy in acute myocardial infarction. N Engl J Med. 2002:346:954-5.), ventricular remodelling-processes that are characterized by the progressive expansion of the area of infarction and the dilatation of the left ventricular cavity lead to the development of cardiac failure in a measurable fraction of the patients, that survived an acute myocardial infarction (Pfeffer M A, Braunwald E. Ventricular remodeling after myocardial infarction. Experimental observations and clinical implications. Circulation. 1990:81:1161-72.). The main goal in order to revert a remodelling would be the stimulation of the neovascularisation as well as the enhancement of the regeneration of cardiac myocytes within the area of infarction.

Recent experiments and clinical studies have shown that the transplantation of specific bone marrow-precursor cells (BMPs) and/or blood-derived circulating precursor cells (BDPs) improves the regeneration following an acute myocardial infarction (Kawamoto A, Gwon H C, Iwaguro H, Yamaguchi J l, Uchida S, Masuda H, Silver M, Ma H, Kearney M, Isner J M, Asahara T. Therapeutic potential of ex vivo expanded endothelial progenitor cells for myocardial ischemia. Circulation. 2001; 103:634-7., Kocher A A, Schuster M D, Szabolcs M J, Takuma S, Burkhoff D, Wang J, Homma S, Edwards N M, Itescu S. Neovascularization of ischemic myocardium by human bone-marrow-derived angioblasts prevents cardiomyocyte apoptosis, reduces remodeling and improves cardiac function. Nat Med. 2001: 7:430-6., Fuchs S, Baffour R, Zhou Y F, Shou M, Pierre A, Tio F O, Weissman N J, Leon M B, Epstein S E, Kornowski R. Transendocardial delivery of autologous bone marrow enhances collateral perfusion and regional function in pigs with chronic experimental myocardial ischemia. J Am Coil Cardiol. 2001; 37:1726-32.). Thus, the cell therapy with bone marrow-stem-/precursor cells is a new option for improving the neovascularisation and the cardiac function in ischemic heart disease. Indeed, it could be shown that the intracoronary infusion of adult precursor cells in patients with acute myocardial infarction is possible and safe, and is associated with significant improvements in the regional and global LV (left ventricular) function. Nevertheless, the particular circumstances of the improvement by the infusion remained unclear. Additionally, for a targeted and effective cell therapy with bone marrow-stem-/precursor cells it is required to ensure that bone marrow-precursor cells (BMPs) and/or blood-derived circulating precursor cells (BDPs) are transplanted that exhibit the highest possible capacity for regeneration, and therefore effectiveness.

It is therefore an object of the present invention to provide an improved method for the diagnosis and/or the prognosis of cardiovascular diseases, for monitoring of their therapies and/or for a stratification for a prospective cell therapy on the basis of bone marrow-precursor cells (BMPs) and/or blood-derived circulating precursor cells (BDPs) for increasing the perfusion of ischemic tissue or for a regeneration of tissue losses in, e.g., cardiac insufficiency.

It is a further object of the present invention to provide a safe method by which bone marrow-precursor cells (BMPs) and/or blood-derived circulating precursor cells (BDPs) can be identified and isolated that are effective and suitable for the cell therapy.

Finally, it is still a further object of the present invention to provide pharmaceutical compositions that comprise bone marrow-precursor cells (BMPs) and/or blood-derived circulating precursor cells (BDPs) that are suitable for the cell therapy and have been isolated according to the invention.

According to a first aspect of the present invention, one object of the invention is solved by an in vitro method for analysing a sample from a mammal in connection with cardiovascular diseases, wherein the method according to the invention method comprises the following steps of: a) isolating of bone marrow-precursor cells (BMPs) and/or blood-derived circulating precursor cells (BDPs) by means of cell specific surface markers, and b) determining/detecting the cardiovascular functionality of the isolated BMPs and/or BDPs by means of a suitable migration assay.

Surprisingly, it could now be found that a relation exists between the capacity for neovascularisation and the capacity of bone marrow-precursor cells (BMPs) and/or blood-derived circulating precursor cells (BDPs), to migrate. This allows for the use of a migration assay as a valuable tool for analysing a sample from a mammal in connection with cardiovascular diseases.

Furthermore, it could now surprisingly be found that in the bone marrow of some donors and/or heart attack patients presumably a dysfunction can be present, whereby those cells that can be taken directly from the bone marrow (BMPs, for example, by punctuation) are limited in their function to be able to form new vessels, and to support the regeneration of the heart. By the assay according to the invention, those donors can be effectively excluded, and at the same time patients with a higher risk can be identified that have a inferior capacity for neovascularisation. Then, these patients can be suitably treated and, in particular, be treated in a preventive and/or supporting manner. Alternatively, by these assays also patients can be identified that would have a higher benefit from a precursor-therapy.

In the context of the present invention, both above indicated characteristics of BMPs and/or BDPs are understood as "cardiovascular functionality".

Vasa et al. (Vasa M. et al., Circ Res Jul. 6, 2001; 89(1):E1-7) describe that the number and migratory activity of circulating endothelial-precursor cells (EPCs) inversely correlates with risk factors for coronary artery diseases (CAD). EPCs of patients with coronary artery diseases exhibit functional impairments. The functional activity of the EPCs is examined based on the migratory capacity with the aid of a migration assay in a Boyden-chamber (migration in the direction of VEGF as "chemo attractant"). The postnatal neovascularisation occurs with the participation of bone-marrow-derived circulating precursor-cells (EPCs), that are derived from haematopoietic stem cells that are characterized by the cell surface marker CD34, or CD133 for less matured cells. The $CD34^+$ cells colonize ischemic areas in mouse models, the injection of $CD34^+$ cells in the experiments promotes the neovascularisation and improves die heart function in these mice. Furthermore, the number and functional activity of EPCs in patients with CAD (coronary artery disease) compared to healthy persons is examined, and also the influence of risk factors on the number and functional activity of the EPCs. The number of $CD34^+$ $KDR^+$ (=VEGF receptor) double positive cells is markedly lower in patients with CAD, compared to healthy persons, nevertheless, the overall number of $CD34^+$ cells, or less differentiated $CD133^+$ cells, is not different in patients and healthy persons. The migratory capacity of the EPCs is reduced in patients with CAD. Vasa et al. suggest that the reduced activity of the EPCs could contribute to a reduced neovascularisation in patients with CAD. Nevertheless, the possibility of a stratification of patients on the basis of an analysis of bone marrow-precursor-cells (BMPs) and/or blood-derived circulating precursor-cells (BDPs) is not mentioned.

Furthermore, Vasa et al. (Vasa M. et al., Circulation, Jun. 19, 2001; 103(24):2885-90) describe an increase of circulating endothelial-precursor-cells (EPCs) by statin-therapy in patients with stable CAD. Thereby, the neovascularisation by EPCs is supported by statins. The functional activity of the EPCs is detected using a migratory assay. Nevertheless, the possibility of a stratification of patients on the basis of an analysis of bone marrow-precursor-cells (BMPs) and/or blood-derived circulating precursor-cells (BDPs) is also not mentioned.

Emerson et al. (in Circulation 2003, 107, 2294-2302) describe that pluripotent stem cells are able to differentiate into cardiomyocytes and endothelial cells. Thus, they can improve the heart function and perfusion in ischemic heart diseases. It is therefore examined, whether bone marrow cells can be safely injected into the heart muscle of patients with the aid of an injection catheter. Further described is the injection of autologous mononuclear bone marrow cells directly into the ischemic area of the left heart chamber of patients with coronary heart disease in a progressed state. The precursor-cells are isolated from the bone marrow by means of a density-gradient-centrifugation, and are characterized using FACS analysis based on different cell surface markers, but not separated. Thereby, according to Tab. 3 of the document haematopoietic precursor-cells are only a minor fraction of the injected cells (ca. 2.5%), whereas T- and B-cells as well as monocytes form the major part. As haematopoietic precursor-cells $CD34^+$ $CD45^{lo}$ cells or $CD133^+$ $CD45^{lo}$ cells are described, respectively. The mononuclear bone marrow cells are examined for "viability" and "clonogenic capacity". The bone marrow cells are injected in saline with heparin and 5% human serum-albumin. Nevertheless, the possibility of a stratification of patients on the basis of an analysis of bone marrow-precursor-cells (BMPs) and/or blood-derived circulating precursor-cells (BDPs) is also not mentioned. Furthermore, no isolated endothelial precursor-cells, but not further fractionated total mono-nuclear bone marrow cells were used.

Kawamoto et al. Circulation 2003, 107, 461-468 describe that endothelial precursor-cells (EPCs) from peripheral blood can be isolated as $CD34^+$ mononuclear cells. In ischemic diseases, EPCs from the bone marrow are mobilised to colonize the region of beginning neovascularisation and to differentiate into mature endothelial cells. It is therefore examined whether the transplantation of precursor-cells directly into the heart muscle promotes the neovascularisation in ischemic tissue. The infusion of autologous precursor-cells directly into the heart muscle increased the neovascularisation in pig-ischemia-models. Furthermore, human precursor-cells were heterologously infunded into the ischemic heart region of rats. For this, human mononuclear $CD34^+$ peripheral blood cells as EPC-enriched cellular fraction are used.

Aicher et al. (Circulation 2003, 107, 2134-2139) describe the colonization of radioactively labelled EPCs in different tissues after infusion into rats. For this, the publication describes a system, wherein human EPCs that are derived from healthy donors, are xeno-transplanted into rats, in which prior an infarction was operatively induced or into control animals without infarction. The isolation of the EPCs is not disclosed, and the classification as $CD34^+$ peripheral blood cells is not mentioned. The cells are cultured, i.e. expanded, and subsequently radioactively labelled with $^{111}$indiumoxine in order to be able to examine the allocation of the EPCs in the acceptor organism after infusion. It is also examined whether the "functional capacity" of the cells after radioactive labelling differs from non-labelled cells. The "functional capacity" is examined using a migration assay, i.e. based on the migration of the cells in the direction of the growth factor VEGF. It is shown that only about 1% of the total infunded cells are forming colonies in the heart. The person of skill thus assumes that the migratory capacity of the EPCs is related to a colonization of the cells in target tissues, possibly also in the area of infarction. Nevertheless, it was not obvious to perform this "quality control" also with non radioactively labelled cells, in particular, since in the publication non-labelled cells were used as a reference.

Finally, Wolfrum et al. (Arterioscler Thromb Vasc Biol 2003, 23, 729-736) generally describe the effect of statins on endothelial cells.

Preferred is a method according to the invention that furthermore comprises the comparison of the result as obtained from the sample as examined with a reference value and/or the result of a reference sample. Such reference values can either be obtained from the patient that is to be individually treated during the progression of the therapy or are the result of large-scale studies. Commonly, a reference value is derived from a so-called healthy control group. The person of skill in this field is readily able to select suitable study protocols in order to obtain suitable reference values.

Preferred is a method according to the invention wherein the sample to be examined is derived from a human. Thereby, the sample to be examined can be selected from the group consisting of bone marrow, peripheral blood or fractions thereof, and cell culture-suspensions or fractions thereof. The selection of the individual sample depends from the kind of the precursor cells to be examined and the method for determining the characteristics of the precursor cells. Further preferably, in case of the withdrawal of blood, a coagulation inhibitor, in particular Heparin or EDTA, is added to the peripheral blood. This facilitates additional processing steps. In a further aspect of the present invention the sample to be examined is obtained from the bone marrow by means of punctuation. This withdrawal represents the basis for obtaining BMP. The further processing according to the invention can comprise an isolation by using density-gradient-centrifugation and/or immunological methods, e.g. immuno magnetic methods, in particular by using FACS. Thereby, according to the invention it is further preferred that the selected specific surface marker for BMP is selected from CD34, CD45, and/or CD133, and the specific surface marker selected for BDP is selected from VEGFR2, CD105, vWF, and/or CD31.

According to a preferred method of the present invention the migration assay is performed in a Boyden-chamber or a modified version thereof. Nevertheless, it will obvious for the person of skill that further methods for determining the migratory capacity can be used without leaving the scope of the present invention. This, in particular, relates to embodiments of the migration assay that are either adapted to the automatisation of the assay and/or its realisation in a "point-of-care"-assay.

Particularly preferred is a method according to the invention, wherein the migration assay is performed by using SDF-1 or VEGF as chemo-attractant for BMP or BDP. As can be taken from the attached experiments, SDF-1 is a preferred stimulator for BMP, and VEGF for BDP. Also, P1GF or MCP-1 can be used.

Voermans et al. (Voermans C, et al. Exp Haematol December 2001; 29(12):1456-64) describe the role of SDF-1 induced migration of haematopoietic precursor cells (CD34 (+)-cells) and a respective migratory assay.

A prerequisite for the success of a cell therapy is the so-called "homing", that is, the targeted migration of cells for colonisation in desired target regions, in particular, if an intravascular route of administration is chosen. It was therefore assumed by the inventors that the migratory capacity of adult precursor cells in the direction of their physiological chemo-attractants could reflect their ability, to migrate into the area of infarction. Indeed, the migration of transplanted cells into the affected tissue and the improvement of the neovascularisation that was induced by the intravenous infusion of human precursor cells, tightly correlates with the SDF-1-induced migratory capacity for BMP and the VEGF-induced migratory capacity for BDP. Nevertheless, these were yet unproven assumptions that were only confirmed in experiments performed the context of the present invention. Is was furthermore unexpected that this migratory capacity is so well-suited as independent predictive factor that diagnostics that are based thereon would provide an improvement in the treatment of CAD. In summary, the improvement of the local contractile myocardial function associated with the functional activity of the infunded precursor-cells discloses a causal relation between the migratory capacity of precursor-cells and the success of a cell therapy in patients with acute myocardial infarction. The invention thus discloses a novel diagnostic method by which an improvement/optimisation of the cell therapy in patients with cardiovascular diseases is made possible. The method allows, based on the determination of the functional activity of precursor-cells, to make reliable predictions, whether the individual will profit from a cell therapy (transplantation of the own precursor-cells) for a regeneration of the destroyed damaged heart muscle tissue, or whether this therapy most likely will not be successful, since the cells have an insufficient capacity to colonize the target tissue.

The methods according to the invention can always be employed in the diagnosis and/or therapy of all cardiovascular diseases, where a therapeutic advantage is expected from a transplantation of precursor cells. Preferred is a method according to the invention, wherein the cardiovascular diseases are selected from the group consisting of stable and unstable angina, stable coronary heart disease, acute coronary syndrome, myocardial infarction, acute myocardial infarction, acute cardiac syndrome, coronary artery disease, chronic ischemic cardiomyopathy (ICMP), dilatative cardiomyopathy (DCM) or other causes of a cardiac insufficiency.

According to a further aspect of the present invention, the method according to the invention can be performed immediately before a cell infusion into the mammal. As already described above, by the assay according to the invention those donors can be effectively excluded and simultaneously patients with a higher risk can be identified that exhibit inferior neovascularisation capacities. These patients can then be suitably treated, and in particular preventive and/or supportive. Alternatively, also patients can be identified by this assay that can have an increased benefit from a precursor-cell therapy. In a further aspect of the method according to the present invention, this relates to a therapy, wherein the examined isolated BMP and/or BDP are autologous and/or heterologous for the patients to be treated, in particular the mammal.

A further aspect of the present invention relates to a diagnostic kit, that in addition to means for performing said method according to the invention contains further suitable components and/or excipients. The kit can consist of one or several separated containers. In particular, suitable components can be manuals or colour charts for aligning of results of measurement based on reference values.

According to the invention the kit is preferably used for the diagnosis and/or the prognosis of cardiovascular diseases, for monitoring of their therapies and/or for a stratification for a prospective cell therapy with stem- and precursor cells for an improvement of the perfusion of ischemic tissue or the regeneration of tissue loss, such as, for example, in heart insufficiency.

A further aspect of the present invention then relates to an in vitro method for isolating of specific bone marrow-precursor cells (BMPs) and/or blood-derived circulating precursor cells (BDPs), wherein the method comprises the steps of a) obtaining a sample from a mammalian donor, b) isolating of (BMPs) and/or (BDPs) by means of cell specific surface marker from the sample so obtained, and c) determining the cardiovascular functionality of the isolated BMPs and/or BDPs by means of a suitable migration assay. It is preferred according to the invention that the sample to be examined is derived from a mammal, in particular the human.

As already mentioned above, the method according to the invention can be employed on all stem- and precursor-cell-populations obtained from a donor, independently from the manner by which the sample is obtained, where it is assumed that they contain suitable BMPs or BDPs. Preferred is a method according to the invention, wherein the sample to be examined is selected from the group consisting of bone marrow, peripheral blood or fractions thereof, and cell culture-suspensions or fractions thereof. Particularly preferred is a method according to the inventions wherein the sample to be examined is obtained from the bone marrow in a suitable manner. It is preferred that the sample to be examined is obtained from the bone marrow by means of punctuation.

Due to the fact that during a withdrawal mostly a heterogeneous admixture of different precursor cells is obtained, a preferred method according to the invention comprises the isolation by means of density-gradient-centrifugation and/or immunological methods. A particularly preferred method for isolation takes place by using FACS or immunomagnetic separation, wherein the cell specific surface marker can be selected for BMP from CD34, CD45 and/or CD133, and can be selected for BDP from VEGFR2, CD105, vWF and/or CD31.

As already mentioned above, in a further aspect of the present invention the migration assay is performed in a Boyden-chamber or in an improvement thereof (see above). Also in this case, it is preferred that the chemo-attractant used for the migration assay is SDF-1, VEGF, P1GF or MCP-1.

An essential aspect of the present invention is the determination of the cardiovascular functionality of precursor cells that were obtained from a particular donor. On the basis of the findings as obtained by means of method according to the invention regarding the utility and efficiency of the obtained precursor cells for the cell therapy, this therapy can be adjusted to the individual patient. As already indicated above, it is assumed that in the bone marrow of particular donor or patients, in particular in patients with ICMB, a dysfunction is present that affects the cardiovascular functionality of the precursor cells. In order to be able to "compensate" in particular cases for these impairments, in a further aspect, the present invention provides a method wherein the isolated BMPs and/or BDPs are further genetically modified, in order to improve the cardiovascular function of the cells. Methods in order to genetically modify BMPs and/or BDPs, and genetic constructs suitable therefore are well-known to the person of skill and can be readily produced and used by him. The exact genetic mechanisms of the impairment of the cardiovascular functionality in certain patients are not yet known, nevertheless the experiments of the present invention resulted in that the migration of the precursor cells derived from these donors is impaired. In order to compensate for these impairments, it would be an approach to transfect the precursor cells with those receptors that are specific for the respective chemo-attractants (in particular SDF-1 for BMP and VEGF for BDP). Thus, one approach would be the transfection of BMP with expression constructs of CXCR4 or constructs that would influence the regulation of CXCR4, from which it was assumed that it would be present downregulated in impaired BMPs. Another approach would be the modification of integrins, such as for example CD49a or other factors, such as for example VCAM-1 or factors interacting therewith.

A further aspect then relates to a specific bone marrow-precursor cell (BMP) or blood-derived circulating precursor cell (BDP) that was produced by means of an above-mentioned method according to the invention. These specific bone marrow-precursor cell (BMP) or blood-derived circulating precursor cell (BDP) according to the present invention can be present as isolated BMPs and/or isolated BDPs for the mammals/patients (that is, the respective acceptor) autologous (own) and/or heterologous (foreign). Naturally, also mixtures of cells are possible.

As already mentioned above the isolated BMPs and/or BDPs can be used in the context of the cell therapy. A further aspect of the present invention therefore relates to a method for the production of a pharmaceutical composition that comprises first a method according to the invention as mentioned above, and furthermore a formulating of the pharmaceutical composition by admixing with common pharmaceutically acceptable carriers and/or diluents. Respective suitable carriers and/or diluents are very well known to the person of skill, and can be very easily adapted to the respective specific applications. Preferably, the precursor cells are infunded beyond the prior implanted stent.

A further aspect of the present invention then relates to a pharmaceutical composition produced according to the present invention. The formulation according to the invention can furthermore be present in admixture with additional pharmaceutically active substances. Thereby, preferred are substances that are selected from aspirin, clopidogel, ACE-inhibitors, betablockers, statines, in particular atorvastatin, erythropoietin and/or VEGF. Other substances are also possible, as long as they to not negatively influence the cardiovascular functionality of the administered precursor cells.

Finally, the present invention relates to the use of a specific BMP and/or BDP according to the invention or a pharmaceutical composition according to the invention for the treatment of cardiovascular diseases, selected from the group consisting of stable and unstable angina, stable coronary heart disease, acute coronary syndrome, myocardial infarction, acute myocardial infarction, acute cardiac syndrome, coronary artery disease, chronic ischemic cardiomyopathy (ICMP), dilatative cardiomyopathy (DCM) or other causes of a heat insufficiency. Thereby preferred is a use according to the invention wherein the treatment comprises the infusion of cells into the mammal. Thereby, as indicated above, other pharmaceutically active substances can also be administered, particularly preferred is a treatment that furthermore comprises the administration of statines, in particular atorvastatin, VEGF, and/or erythropoietin.

Recently performed experiments by the inventors showed that the migratory capacity of the precursor cells of patients with CAD correlated (r=0.783; p=0.001; n=11) very strictly with the neovascular improvement following transplantation in nude mice after rear limbischemia. Thus, the inventors concentrated on the measuring of the migratory capacity of the transplanted precursor cells, immediately before the intracoronary infusion into patients with acute myocardial infarction, in order to relate the functional characteristics of the transplanted precursor cells with quantitative results of the outcome after 4 months. The results showed that the migratory capacity of the infunded precursor cells predicted an improvement of the LV ventricular pumping function, and a reduction of the size of infarction, suggesting a causal relation between the migratory capacity of the precursor cells and the regeneration of the cardiac function after a cell therapy in patients with acute myocardial infarction with damaged myocardium.

The present invention thus shows for the first time that the functional capacity of the transplanted precursor cells is a mainly independent determinant of the subsequent improvement in the regional left ventricular function, and predicts a reduction of the area of infarction following intracoronary cell transplantation. Interestingly, the functional activity of the cells, as determined by their migratory activity, was more informative than the cellular count. In summary, these data for the first time describe a causal relation between precursor-cell therapy and the improvement of the left ventricular pumping function/ventricular regeneration in patients after myocardial damage.

Prior experimental examinations suggested that the improvement in the ventricular function following experimentally induced myocardial infarction is due to a stimulated neoangiogenesis which leads to late myocardial remodelling by increased myocardial bloodflow, rescue of resting myocardium, the reduction of the myocardial fibrosis and the reduced apoptosis of hypertrophic myocytes in the peri-infarction region (Kawamoto A, Gwon H C, Iwaguro H, Yamaguchi J l, Uchida S, Masuda H, Silver M, Ma H, Kearney M, Isner J M, Asahara T. Therapeutic potential of ex vivo expanded endothelial progenitor cells for myocardial ischemia. Circulation. 2001; 103:634-7., Kocher A A, Schuster M D, Szabolcs M J, Takuma S, Burkhoff D, Wang J, Homma S, Edwards N M, Itescu S. Neovascularization of ischemic myocardium by human bone-marrow-derived angioblasts prevents cardiomyocyte apoptosis, reduces remodeling and improves cardiac function. Nat Med. 2001: 7:430-6., Takahashi T, Kalka C, Masuda H, Chen D, Silver M, Kearney M, Magner M, Isner J M, Asahara T. Ischemia- and cytokine-induced mobilization of bone marrow-derived endothelial progenitor cells for neovascularization. Nat Med. 1999:5:434-8., Murohara T, Ikeda H, Duan J, Shintani S, Sasaki K, Eguchi H, Onitsuka I, Matsui K, Imaizumi T. Transplanted cord blood-derived endothelial precursor cells augment postnatal neovascularization. J Clin Invest. 2000:105: 1527-36.). In addition, it was reported that the intramyocardial injection of BMPs led to a regeneration of significant amounts of contracting myocardium, suggesting that the novel generation of myocardium can lead to an improvement of the outcome of myocardial infarction following the local administration of adult precursor cells. Indeed, it could be recently shown by the inventors that BDPs remain their ability to trans-differentiate into functional cardiac myocytes (Badorff C, Brandes R P, Popp R, Rupp S, Urbich C, Aicher A, Fleming I, Busse R, Zeiher AM, Dimmeler S. Transdifferentiation of blood-derived human adult endothelial progenitor cells into functionally active cardiomyocytes. Circulation. 2003:107:1024-32.). This also holds true for BMPs (Orlic D, Kajstura J, Chimenti S, Jakoniuk I, Anderson S M, Li B, Picket J, McKay R, Nadal-Ginard B, Bodine D M, Leri A, Anversa P. Bone marrow cells regenerate infarcted myocardium. Nature. 2001 ; 410:701 -5.).

Obviously, the present study can not disclose the cell mechanisms that are associated with the improved left ventricular remodelling-processes that occur following to a precursor cells-therapy. Nevertheless, a recent study that was performed in patients with rear limb-ischemia showed that the intramuscular injection of precursor cells into the gastrocnemical muscle led to a significant improvement at the rear limb-perfusion (Tateishi-Yuyama E, Matsubara H, Murohara T, Ikeda U, Shintani S, Masaki H, Amano K, Kishimoto Y, Yoshimoto K, Akashi H, Shimada K, Iwasaka T, Imaizumi T. Therapeutic angiogenesis for patients with limb ischaemia by autologous transplantation of bone-marrow cells; a pilot study and a randomised controlled trial. Lancet. 2002; 360: 427-35.). In agreement with the fact that an intracoronary infusion of precursor cells was associated with an improvement of the perfusion index in the target area, these data show that the colonialization of the precursor cells into the area of infarction can lead to an improved neovascularisation, which can lead to a reduction of LV-dilatation and to a maintenance of the contractile performance by rescue of resting myocardium, the reduction of myocardial fibrosis, and apoptosis in the peri-infarction region. In addition, immigrated precursor cells can not only release a multitude of angiogenetic growth factors, whereby endogenous neovascularisation processes in the border zone of infarction are amplified, but also release factors that attract circulating or tissue-resident heart-precursor cells, whereby endogenous repair mechanisms of the myocardium are amplified. Finally, although the number of infunded precursor cells did not predict the following functional improvement, we can not exclude the possibility that resident precursor cells have possibly differentiated into functionally active cardiomyocytes, which would lead to a regeneration of significant amounts of contracting myocardium. Comparisons between the transplantation of contractile versus non-contractile cells in experimental studies showed that the improvement of the ventricular contraction was specifically dependent from contractile cells, whereas the ventricular dilatation was improved independently from the type of cell (Hutcheson K A, Atkins B Z, Hueman M T, Hopkins M B, Glower D D, Taylor D A. Comparison of benefits on myocardial performance of cellular cardiomyoplasty with skeletal myoblasts and fibroblasts. Cell Transplant. 2000; 9:359-68., Sakai T, Li R K, Weisel R D, Mickle D A, Jia Z Q, Tomita S, Kirn E J, Yau T M. Fetal cell transplantation: a comparison of three cell types. J Thorac Cardiovasc Surg. 1999; 118:715-24.). In the present study, the systolic function was markedly improved, which is in agreement with the experimental results following the transplantation of bone-marrow derived angioblasts (Kocher A A, Schuster M D, Szabolcs M J, Takuma S, Burkhoff D, Wang J, Homma S, Edwards N M, Itescu S. Neovascularization of ischemic myocardium by human bone-marrow-derived angioblasts prevents cardiomyocyte apoptosis, reduces remodeling and improves cardiac function. Nat Med. 2001:7:430-6.).

In summary, the invention discloses the migratory capacity of precursor cells as a major and independent determinant in order to predict a functional improvement and reduction of the area of infarction following the intracoronary infusion of adult precursor cells after cell therapy. Furthermore, the invention allows for an improvement of the functional capacity of adult precursor cells before a transplantation, in order to further improve the cardiac regeneration following ischemic injury.

The data of the present study furthermore show that mononuclear cells that have been isolated from the bone marrow of patients with ischemic cardiomyopathy exhibited a significantly reduced activity in the support of the neovascularisation in nude mice following induction of interrupt-rear limb ischemia. Thus, the functional capacity of BMP, as determined via their colony forming activity and their migratory response on SDF-1 in BMP that were isolated from patients with ICMP, was significantly reduced. The injection of these BMPs from patients with ICMP into mice with rear limb-ischemia showed a significantly reduced ability to reconstitute the rear limb-perfusion after unilateral ligation of the femoral artery. It can be concluded therefrom that the reduced functional activity limits the potential for neovascularisation of BMPs from patients with ICMP. The functional impairment of BMPs from patients with ICMP can also limit their therapeutic potential for the medical cell therapy, in particular, if an intravascular route of administration is used which requires that the precursor cells extravasate against a gradient of a chemo-attractant, in order to migrate into ischemic tissue. The monitoring of the migratory and colony forming activities of precursor cells before the therapy can serve as a surrogate for the identification of patients that could gain a larger benefit from the cell therapy. On the other side, a recent experimental study suggests that fully functional BMPs from healthy donor mice can reconstitute the age-related host-cardiac angiogenesis in a mouse model of impaired neovascularisation. Thus, it is tempting to speculate that a pharmacological or genetic manipulation of the functionally impaired BMPs before an infusion can improve their functional activity, and subsequently improve the therapeutic benefit of the patient from the therapy.

The invention shall now be further described in den following examples with reference to the attached Figures, nevertheless, without being limited thereto. In the Figures

EXAMPLES

Patients

Patients between 18 and 75 years were included into the study, if they had a first acute ST-elevation myocardial infarction that was acutely treated by a coronary stent with GPIIb/IIIa blocking. Exclusion criteria were the presence of cardiogenic shock (defined as systolic blood pressure <80 mmHg, which required intravenous pressers or intra-aorta balloon-antipulse), strong bleedings that required blood transfusion after acute reperfusion treatment, history of leucopoenia, thrombocytopenia, hepatic or renal dysfunction, signs of malign diseases or unwillingness for participation. The ethics committee of the Universitaetsklinikum of Johann Wolfgang Goethe Universitaet in Frankfurt, DE, approved the protocol of the study as performed, and the study was performed in agreement with the declaration of Helsinki. Written informed consent was obtained from each patient.

As an internal reference group reflecting the standard of care that was provided at the hospital, 15 patients were chosen that were matched for ejection fraction, location of infarction and size of infarction with the study population, in which an acute reperfusion therapy by stent-implantation was performed, and for which acute- and 4 months follow-up-paired LV-angiograms were available.

Protocol of the Study as Performed

The study protocol was described earlier (Assmus B, Schachinger V, Teupe C, Britten M, Lehmann R, Dobert N, Grunwald F, Aicher A, Urbich C, Martin H, Hoelzer D, Dimmeler S, Zeiher A M. Transplantation of Progenitor Cells and Regeneration Enhancement in Acute Myocardial Infarction (TOPCARE-AMI). Circulation. 2002; 106:3009-17.). Briefly, patients were randomly grouped for the receipt of an intercoronary infusion of either bone marrow-precursor cells (BMP) and/or blood-derived circulating precursor cells (BDP) 4 days following AMI.

In patients that received the bone marrow-precursor cells (BMPs) 50 ml bone marrow-aspirate were obtained in the morning of the day of cell transplantation. Bone marrow-derived mono-nuclear cells (BMCs) were obtained by density-gradient-centrifugation. After two washing steps the cells were resuspended in 10 ml X-vivo 10 medium (Biowhittaker). The cellular suspension consisted of heterogeneous cell populations that, in addition to haematopoietic precursor cells that were detected by FACS-analysis by using directly conjugated antibodies against anti-human CD34 (FITC, Becton Dickinson), anti-CD45 (Becton Dickinson), CD14 (BD Pharmingen, San Diego, US), CXCR4 (BD Pharmingen), CD49d (BD Pharmingen) and CD133 (Miltenyi Biotech, Bergisch Gladbach, DE), also contained other cell-types (e.g. side population-cells, stromal cells, etc.). In total, a mean value of $5.5 \pm 3.6 \times 10^6$ CD34/CD45-positive cells (in $219 \pm 82 \times 10^6$ mononuclear cells) per patient was infunded.

In patients that received the blood-derived circulating precursor cells (BDP) 250 ml of venous blood was collected immediately after the random grouping (24 hours following the AMI). Mononuclear cells were suspended in X-vivo-15 medium (Biowhittaker, Apen, DE), supplemented with 1 ng/ml carrier-free human recombinant VEGF (R&D, Wiesbaden, DE), 0.1 µM Atorvastatin (Pfizer, Freiburg, DE) and 20% human serum, withdrawn from each individual patient. The cells were seeded in a density of $6.4 \times 10^5$ cells/mm² on fibronectin-coated dishes (Roche, Grenzach, DE). After 3 days of culture, the cells were washed away with 0.5 mM EDTA, washed twice, and resuspended in a final volume of 10 ml X-vivo 10 medium. The cell suspension as obtained (mean of the injected cells $17 \pm 12 \times 10^6$) contained a heterogeneous population of precursor cells. Nevertheless, more than 90% of the cells exhibited endothelial characteristics, as was shown by Dil-acetylated LDL-uptake and lectin binding and the expression of typical endothelial marker proteins including VEGFR2 (KDR) (ReliaTech, Braunschweig, DE), Endoglin (CD105) (NeoMarkers, Asbach. DE), von Willebrand factor (vWF) (Oncogene, Schwalbach, DE) and platelet endothelial cell-adhesion molecule-1 (PECAM-1/CD31) (Dianova, Hamburg; Assmus B, Schachinger V, Teupe C, Britten M, Lehmann R, Dobert N, Grunwald F, Aicher A, Urbich C, Martin H, Hoelzer D, Dimmeler S, Zeiher A M. Transplantation of Progenitor Cells and Regeneration Enhancement in Acute Myocardial Infarction (TOPCARE-AMI). Circulation. 2002; 106:3009-17., Dimmeler S, Aicher A, Vasa M, Mildner-Rihm C, Adier K, Tiemann M, Rutten H, Fichtlscherer S, Martin H, Zeiher A M. HMG-CoA reductase inhibitors (statins) increase endothelial progenitor cells via the PI 3-kinase/Akt pathway. J din Invest. 2001; 108:391-7., Vasa M, Fichtlscherer S, Aicher A, Adler K, Urbich C, Martin H, Zeiher A M, Dimmeler S. Number and migratory activity of circulating endothelial progenitor cells inversely correlate with risk factors for coronary artery disease. Circ Res. 2001; 89:E1-7., Vasa M, Fichtlscherer S, Adier K, Aicher A, Martin H, Zeiher A M, Dimmeler S. Increase in circulating endothelial progenitor cells by statin therapy in patients with stable coronary artery disease. Circulation. 2001 ,-103:2885-90.).

The cells were infunded via an over-the-wire balloon catheter that was projected into stent that was implanted earlier during the method of the acute, and inflated with low pressure, in order to completely block the blood flow for 3 minutes in order to allow for an adhesion and potential transmigration of the infunded cells by the endothelium. This procedure was repeated for 3 times in order to allow for the infusion of the total 10 ml precursor cells, separated by 3 minutes of reflux by deflation of the balloon in order to minimise an extensive ischemia. Following completion of the intracoronary cell transplantation, a coronary angiography was repeated in order to ensure the opening of vessels and an unrestricted flow of the contrast material.

Detection of the Migratory Capacity of Transplanted Precursor Cells

A sample of precursor cells was resuspended in 500 µl endothelial-base medium (EBM, Cell Systems) immediately before intracoronary cell infusion, counted, and $2 \times 10^4$ cells were placed in the upper chamber of a modified Boyden-chamber. Then, the chamber was placed into a 24-well culture dish which contained EBM and either 50 ng/ml VEGF for measuring the migratory capacity of circulating blood-derived cells or 100 ng/ml SDF-1 for measuring the migratory capacity of bone-marrow-derived precursor cells. After 24 hours of incubation at 37° C. the bottom surface of the filter was washed with PBS, and fixed with 2% para-formaldehyde. For measuring the cellular nuclei were stained with DAPI. Cells that migrated into the lower chamber were manually counted in 5 random microscopic fields by a blind examiner (Vasa M, Fichtlscherer S, Aicher A, Adler K, Urbich C, Martin H, Zeiher A M, Dimmeler S. Number and migratory activity of circulating endothelial progenitor cells inversely correlate with risk factors for coronary artery disease. Circ Res. 2001; 89:E1-7., Asahara T, Takahashi T, Masuda H, Kalka C, Chen D, Iwaguro H, Inai Y, Silver M, Isner J M. VEGF contributes to postnatal neovascularization by mobilizing bone marrow-derived endothelial progenitor cells. Embo J. 1999; 18:3964-72.).

Assay for Colony Forming Units

BMPs ($1 \times 10^5$ per dish) were seeded onto methylcellulose-plates (Methocult GF H4535) that contained stem cell factor, G-CSF, GM-CSF, interleukin-3, interleukin-6, CellSystems, St. Katharinen, DE). The plates were examined under phase contrast microscopy and colony forming units of granulo-cyte-macrophages (CFU-GM; colonies) were counted after 14 days incubation by two different researchers.

Left-Ventricular Angiography

LV-angiograms were obtained according to standard-recording-guidelines. The LV-ejection-fractions and -volumes were calculated by using the area-length-method (Dodge H T Sh, Ballew D W, et al. The use of biplane angiography for the measurement of left ventricule volume in man. Eur Heart J. 1960; 60:762-776.), and the regional movement of the wall was determined by means of using the centreline-chord-method (Sheehan F, Bolson E, Dodge H, Mathey D, Schofer J, Woo H. Advantages and applications of the centreline method for characterizing regional ventricular function. Circulation. 1986; 74:293-305.).

Statistical Analysis

Continuous variables are given as mean±SD. Categorical variables were compared with the Chi-Square-test or Fischer's exact test. The statistical comparison between initial and follow-up data were performed in a non-parametric manner using the paired signal-test. The linear non-parametric correlation was calculated using the Spearman correlation. The multivariate analysis was performed using the linear regression model. A statistical significance was assumed, if p<0.05. All statistical analyses were performed using SPSS (Version 11.0, SPSS Inc.).

The demographic, clinical and angiographical characteristics of the study population are shown in Table I. There was no significant difference in any of the baseline-parameters.

Effects of Precursor-Cell Therapy on the LV Function

Figure 1A:
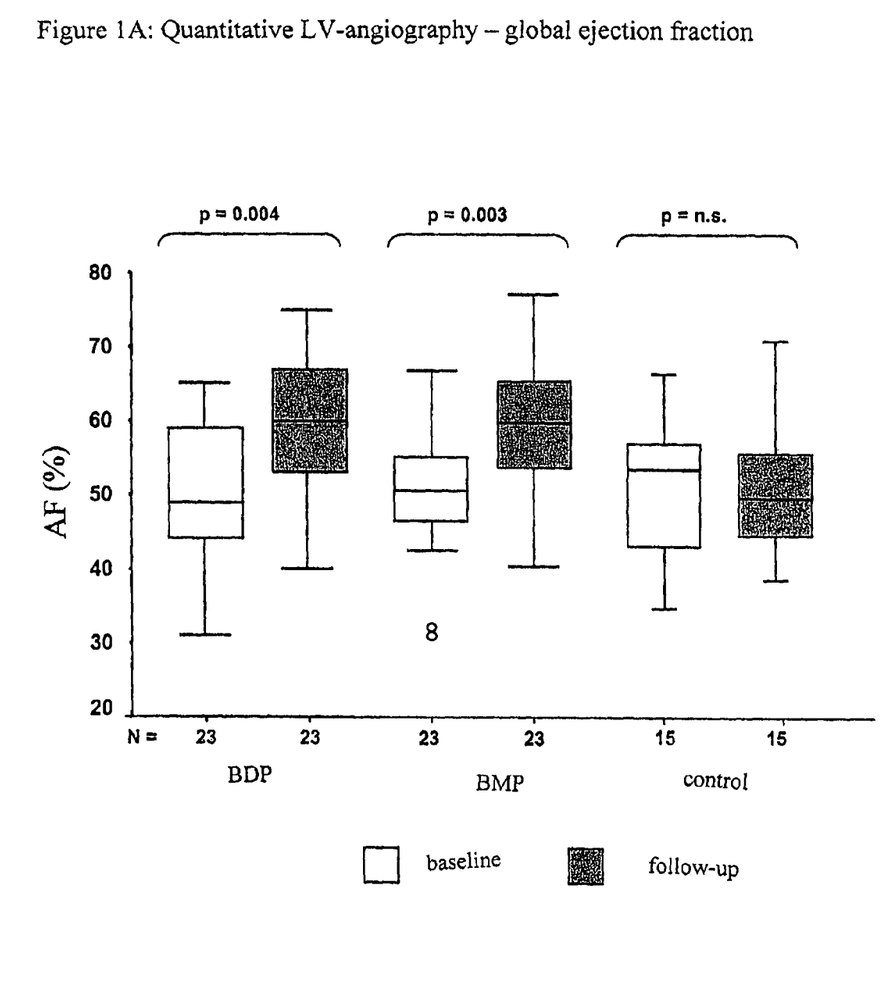
FIG. 1 shows the quantitative left ventricular angiography that shows the ejection fraction (A), end-systolic and end-diastolic volumes (B), at base line and follow-up for patients that received circulating blood-derived (BDP) or bone marrow-derived (BMP) precursor cells, and for patients of the non-randomised control group.
Figure 1B:
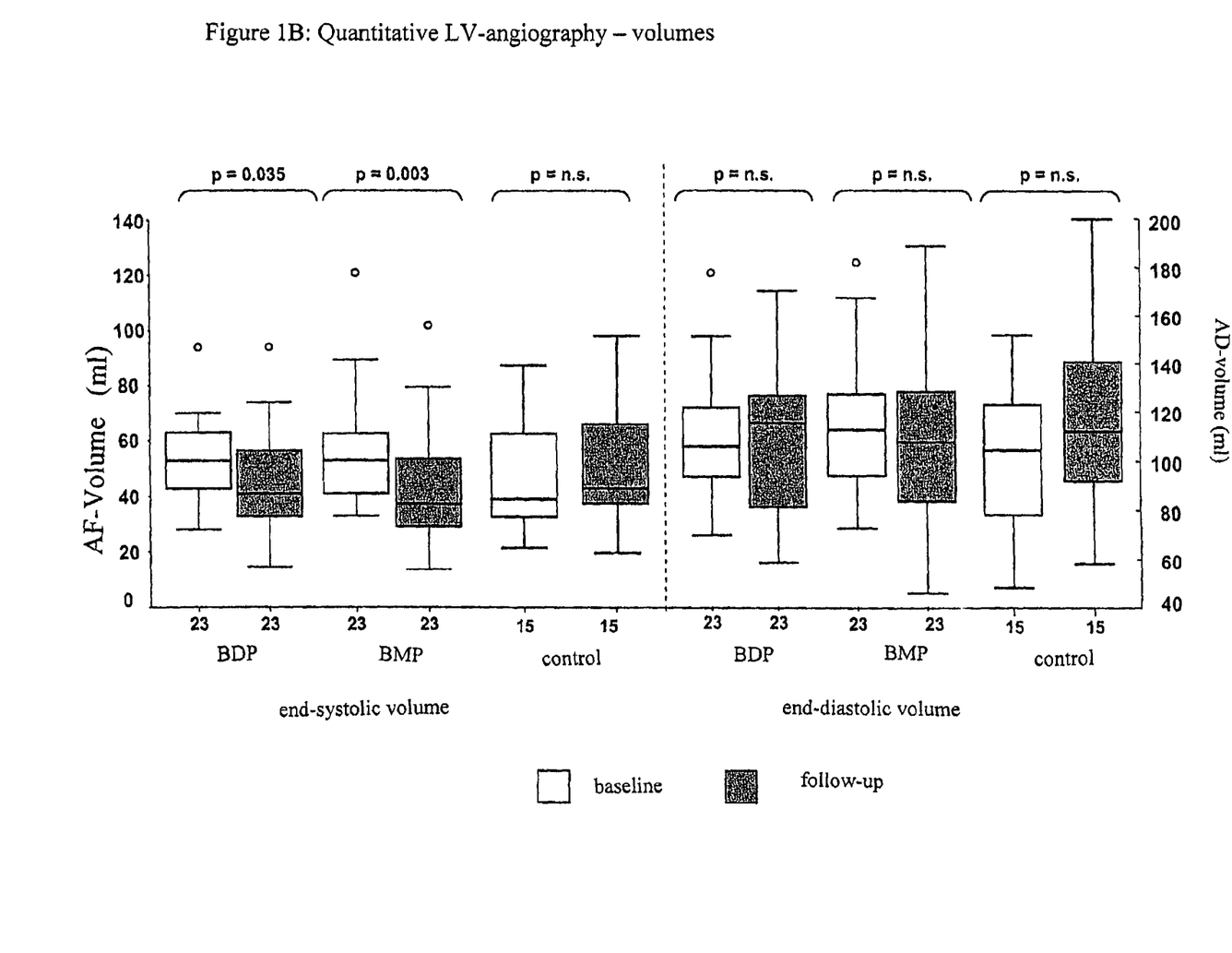

FIG. 1 and Table I show the LV-ejection-fraction, the end-systolic and end-diastolic LV-volumes before and 4 months after intracoronary precursor cell-infusion. The transplantation of precursor cells was associated with a profound improvement of the LV-ejection-fraction of 49.2±10% to 58.3±10% (p<0.001, FIG. 1A) and a significant reduction of the LV end-systolic-volume of 55.2±18 ml to 44.1±19 ml (p=0.009, FIG. 1B), irrespectively of the infunded cell type. A detailed analysis of the regional wall movement resulted the most pronounced improvement in the border region that as adjacent to the central area of infarction (Table 2).

In contrast to this, in the reference group of patients that did not receive a precursor-infusion, but, otherwise, were treated identically, no significant changes could be detected (FIG. 1 and Table 2). Thus, despite similar starting values, in the reference group the improvement in the global LV-ejection-fraction was significantly lower (p=0.024) and the end-systolic LV-volume rather increased after 4 months (p=0.002).

The improvement of the LV-function in the precursor-cell-treated patients was confirmed by echocardiography and was maintained in those patients that intermediately were subjected to a 12 month follow-up (BDP n=14, BMP n=10). No one of these patients experienced any malign arrhythmia during follow-up.

Figure 2:
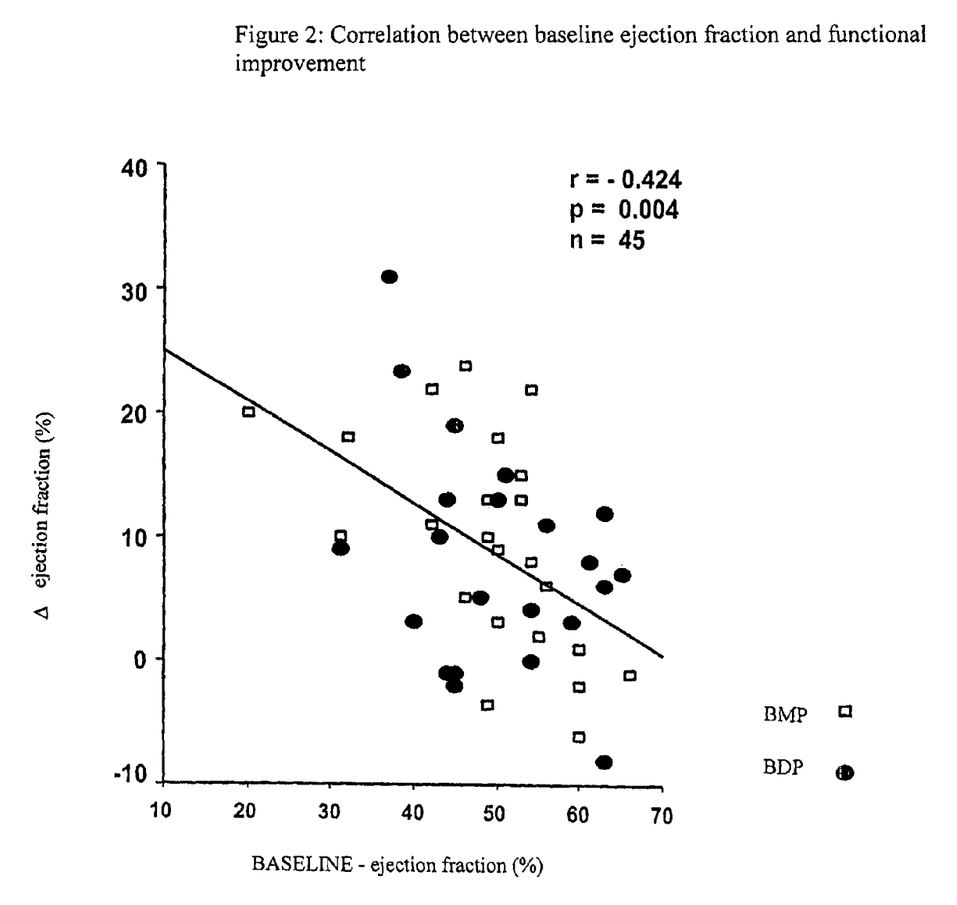
FIG. 2 shows the correlation between base line left ventricular ejection fraction and improvement in the ejection fraction with the regression line for the overall study group.

Figure two shows that there was a strict inverse correlation between baseline LV-ejection fraction and improvement in the ejection fraction during the 4 months follow-up, indicating that those patients with the severest impairment in the LV-function had the largest benefit in view of the improvement of the ejection fraction, independently from the infunded cell type.

Effects of the Precursor-Cell Therapy on the Size of Infarction, Measured by MRI Those 26 patients that were subjected to a serial initial MRI and after 4 months follow-up, and did not differ from the overall study in view of the improvement in the LV-ejection fraction (from 50.7±8% to 60.5±8%, p<0.001) or the reduction in the end-systolic LV-volume (from 53.7±17 ml to 40.8±15 ml, p<0.002). Importantly, an intracoronary precursor-cell-infusion with a significant reduction in the volume of the late-amplification from 39.3±34 to 31.6±28 ml, p<0.038 was present, indicating a significant reduction of the size of infarction. Again, there were no significant differences between patients that received BDP compared to BMP-patients.

Number and Migratory Capacity of Transplanted Precursor Cells

The absolute number of the infunded precursor cells did not correlate with an improved global or regional LV-function or with the reduction of the size of infarction, if the overall cell counts or subgroups (e.g. CD34/CD45 or CD34/CD133 positive cells) were used (global ejection fraction: BDP: r=−0.73, p=0.2; BMP: r=−0.147, p=0.517; infarction size: BDP: r=−0.187, p=0.5; BMP: r=−0.084, p=0.776). No significant differences were found in the functional improvement when the cell counts were dichotomised.

Figure 3:
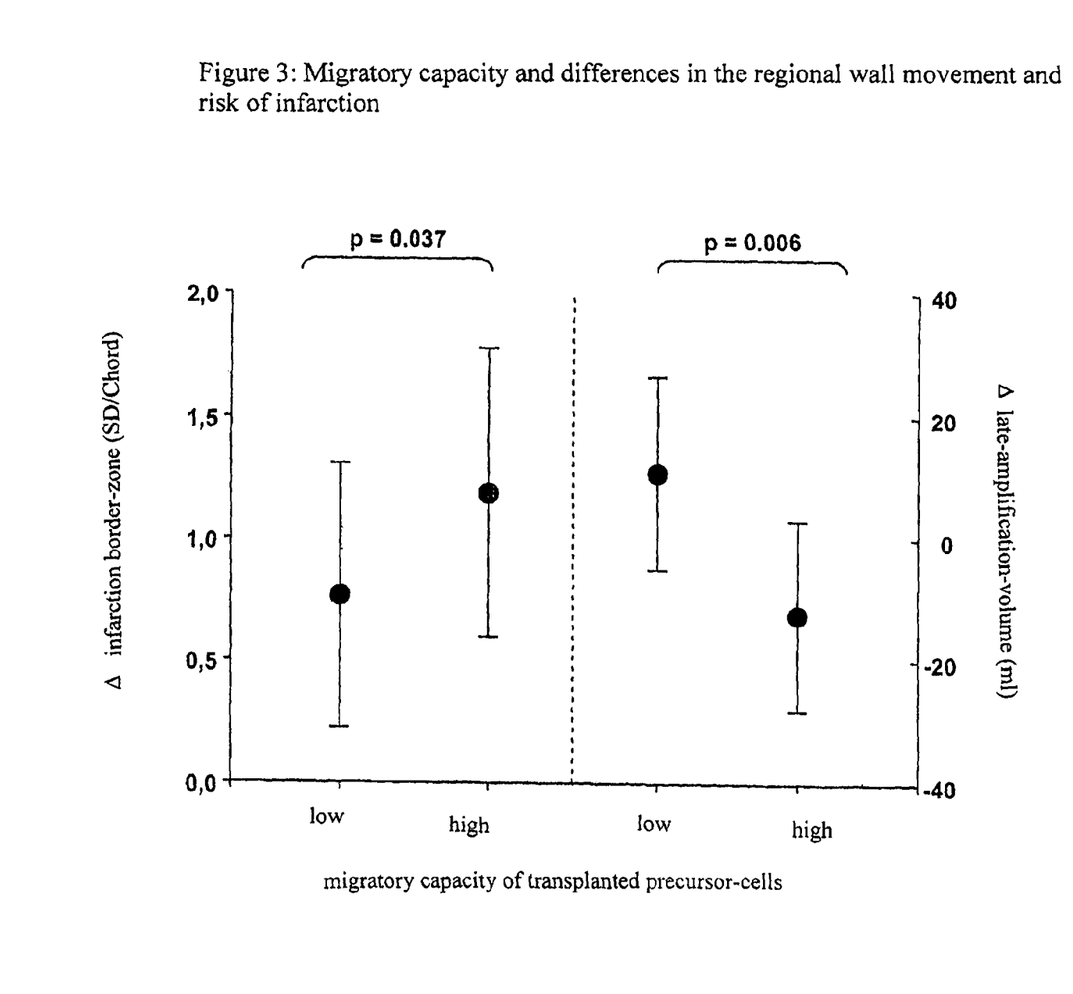
FIG. 3 shows the mean value of the functional improvement and the reduction of the size of infarction for patients that shows precursor cells either with lower or higher migratory capacity.

In contrast to this, the dichotomisation of the precursor cells migratory capacity into those above and below of the mean value that patients that received cells with a high migratory capacity showed a significant improvement of the regional LV-function as was shown by quantitative LV-angiography in the border zone of the area of infarction, compared to patients which received precursor cells with lower migratory capacity (FIG. 3). As depicted in Figure three the absolute reduction in the late-amplification was significantly higher in patients that received cells with a higher migratory capacity, compared with those that received precursor cells with lower migratory capacity.

Nevertheless, neither the clinical variables nor the functional parameter before the cell transplantation, such as e.g. global LV-ejection fraction, LV end-diastolic and end-systolic volumes or the regional LV-function between both groups at the start line were different (Table 3), which therefore excluded any potential further effects of the severity of the disease on the cell-migratory activity at baseline.

Multivariate Analysis of Independent Prediction-Factors of the Functional Improvement and Reduction of the Size of Infarction In order to identify independent predictive factors of the functional improvement and reduction of the size of infarction following intracoronary precursor-cell-infusion into the infarction artery in patients with acute myocardial infarction the inventors performed a multivariate analysis that included all parameters that were statistically significant or were nearly statistically significant by univariate analysis or from which it was known that they influence the LV-function or size of infarction. As shown in Table 4A, the migratory capacity of the transplanted precursor cells remained strongest statistically significant independent predictive factor of the reduction of the size of infarction, as was measured by the reduction of the late-amplification volume. The only other predictive factor was the baseline-ejection fraction, whereas neither the initial size of infarction, nor the age, gender or the time to revascularisation remained independent predictive factors. Likewise as summarized in Table 4B the migratory capacity also independently predicted the regional LV-functional improvement. Thus, the migratory capacity of the infunded cells is a major independent determinant of the functional improvement and reduction of the size of infarction subsequent to the precursor cell-therapy in patients with acute myocardial infarction.

Number and Migratory Capacity of BMPs

The characteristics and functional activity of BMPs were examined by using of bone marrow aspirates of 18 patients with ICMP and 8 total volunteers. The baseline-characteristics of the study populations are depicted in Table 5.

Figure 4:
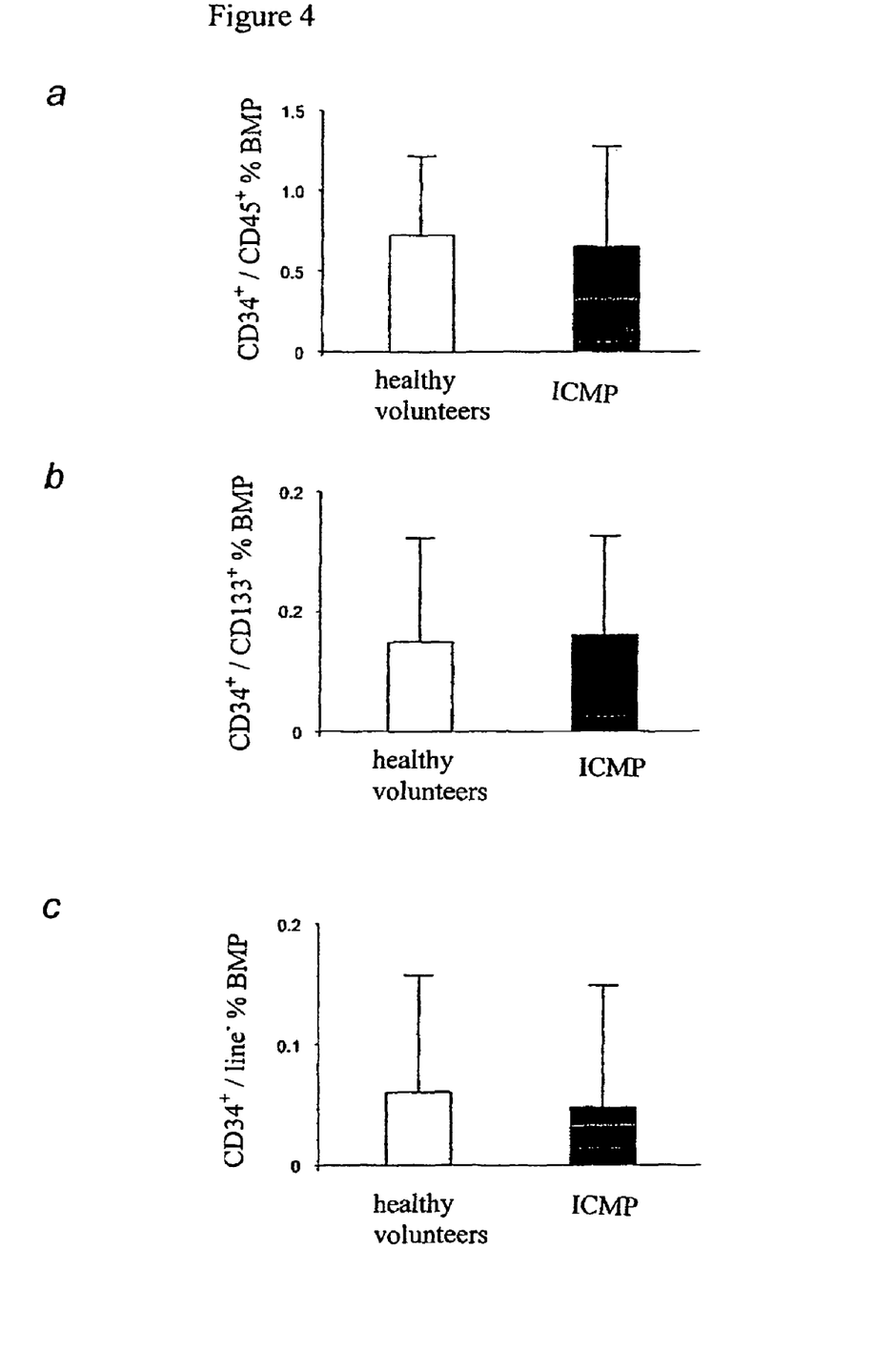
FIG. 4 shows the flow cytometry analysis on precursor cell marker in BMP from the healthy controls and patients with stable ischemic cardiomyopathy. a-c, no significant differences were observed between the two groups.

In order to examine if the number of precursor cells was reduced with respect to BMPs in patients with ICMP, compared to the overall control, the number of haematopoietic precursor cells was determined that is characterized by the expression of the marker protein CD34. The number of CD34+/CD45+ were similar both in the healthy control as well as in patients with ICMP (FIG. 4). In addition, also the immature subsets of haematopoietic precursor cells that were defined as CD133+/CD34+ cells and non-assigned line-/CD34+ did not differ between the groups (FIG. 4).

Figure 5:
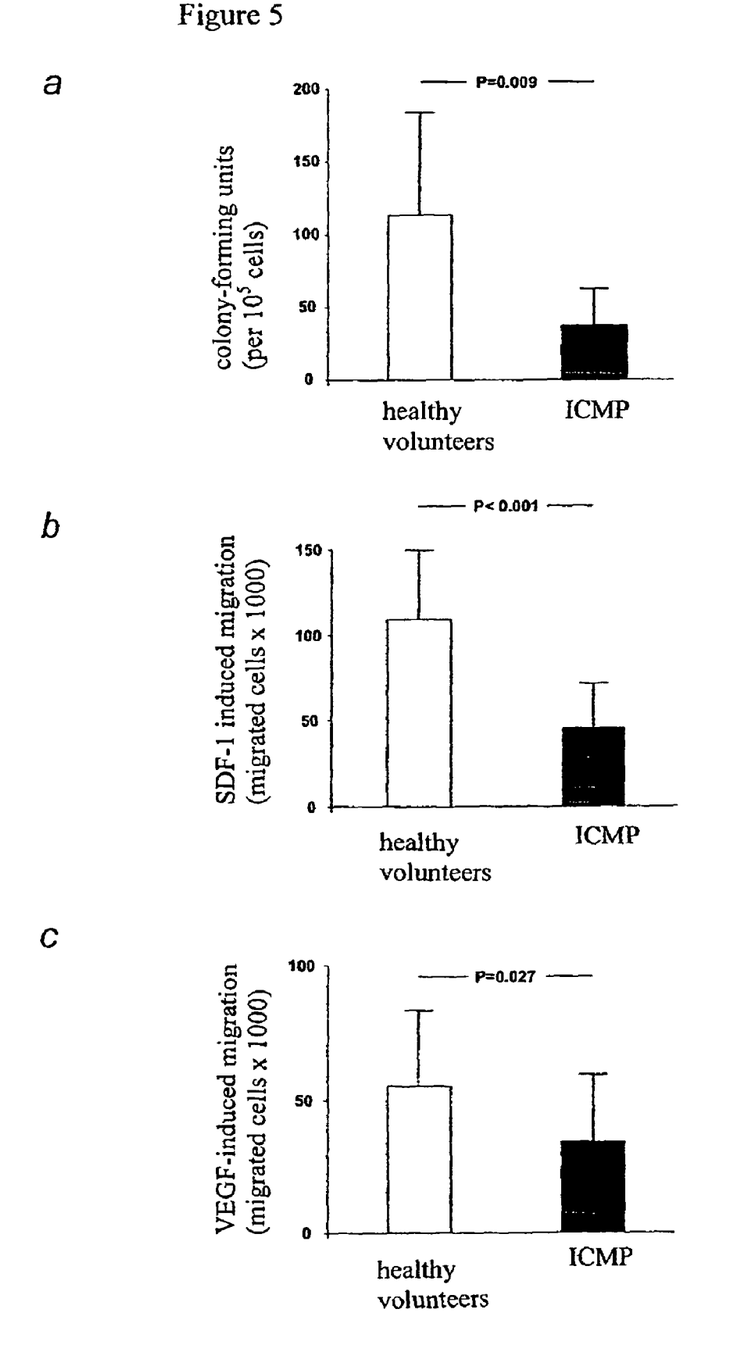
FIG. 5 shows the functional activity of the BMPs from den healthy controls and patients with stable ischemic cardiomyopathy. a, Colony-forming units per $5 \times 10^5$ BMPs were determined after 14 days. b, The migratory capacity of the BMPs in response to stromal cell-derived factor 1 (SDF-1) and c, Vascular endothelial growth factor (VEGF) were measured using the BioCoat® invasion assay. d, Correlation between SDF-1 induced migration and colony-forming capacity and e, Correlation between VEGF induced migration and colony-forming capacity.

The activity of precursor cells in bone marrow aspirates was furthermore determined by measuring the colony-forming activity and migration. Interestingly, BMPs from patients with ICMP showed a significantly reduced number of colony-forming units, compared to BMP from the healthy control (37.3×25.0 CFU-GM/dish versus 113.8×70.4 CFU-GM/dish, p=0.009) (FIG. 5a). The migratory response for SDF-1 and VEGF was also significantly reduced in the BMPs of patients with ICMP, compared to BMPs from the healthy control (VEGF: 34±24.2 versus 54.8±29.3 cells/microscopic field; p=0.027; SDF-1: 46.3±26.2 versus 108.6±40.4 cells/microscopic field; p=0.001) (FIGS. 5b and c). Correspondingly, the colony-forming capacity correlated closely with the migratory response for SDF-1 (r=0.65; p<0.001) (FIG. 5d).

Independent Predictive-Factors for the Functional Activity of BMPs

The SDF-1 induced migration, but not the basal migration or the VEGF-induced migration correlated with the functional improvement of the neovascularisation in the rear-limb ischemia-model (r=0.78; p<0.001) (FIG. 6). The colony-forming activity of the BMP was also significantly associated with the neovascularisation-capacity of the cells (r=0.74; p<0.001). Different clinical baseline characteristics of the patients were also associated with the therapeutic effect of the BMPs in the mouse model of rear-limb ischemia (Table 6, left column), but all variables except for the SDF-1 induced migration lost their statistical significance, when the analysis was limited to patients with ICMP (Table 6, right column).

For a prediction of a threshold-value of the functional improvement of the neovascularisation ng for a preparation of the BMPs as described above, exemplarily a potential threshold-value was determined that based on SDF-1 and VEGF resulted in the following values:

TABLE A

| | migration of BMPs | | |
|---|---|---|---|
| | | migration SDF (×1000) | migration VEGF (×1000) |
| N | valid | 82 | 83 |
| | lacking | 253 | 252 |
| median percentile | | 70.2500 | 43.0000 |
| 25 | | 38.1250 | 22.0000 |
| 33.333 | | 47.6667 | 25.0000 |
| 50 | | 70.2500 | 43.0000 |
| 66.666 | | 104.0000 | 78.2500 |
| 75 | | 120.7500 | 96.0000 |

The numbers indicate how many of the cells of the 500,000 cells as employed have transmigrated within 24 h. 100×1000 thus mean that 20% of the cells have transmigrated.

For a prediction of a threshold-value of the functional improvement of the neovascularisation ng for a preparation of the BDPs as described above, exemplarily a potential threshold-value was determined that based on VEGF resulted in the following values

TABLE B

| | migration of BDP | |
|---|---|---|
| | | migration VEGF (×1000) |
| N | valid | 120 |
| | lacking | 215 |
| median percentile | | 4.8500 |
| 25 | | 2.2250 |
| 33.333 | | 2.8667 |
| 50 | | 4.8500 |
| 66.666 | | 7.7667 |
| 75 | | 10.7000 |

For BMP an acceptable (preferred) threshold-value based on the median in the test with SDF-1 thus would be 70×1000 migrated cells (i.e., ca. 14%). For BMP a further acceptable (preferred) threshold-value based on the median in the test with VEGF thus would be 43×1000 migrated cells (i.e., ca. 8.6%).

In contrast, for BDP an acceptable (preferred) threshold-value based on the median in the test with VEGF 4.85×1000 migrated cells (i.e., ca. 1%).

Despite the fact that not all cell-populations migrate identically, based on the overall migration of all cells thus information can be gained regarding the fact, how well the cells of the patient migrate, and whether these are suitable.

TABLE 1

Demographic, clinical and angiograpic characteristics of the study population

|  | BDP group | PMP group | control (non randomised) | p-value |
|---|---|---|---|---|
|  | n = 23 | n = 23 | n = 15 | n.s. |
| age (years) | 50 ± 10 | 52 ± 10 | 54 ± 13 | n.s. |
| male gender (%) | 87 | 86 | 80 | n.s. |
| hypertension (%) | 57 | 48 | 60 | n.s. |
| hyperlipidaemia (%) | 7 | 60 | 80 | n.s. |
| diabetes (%) | 17 | 27 | 7 | n.s. |
| smoker (%) | 83 | 91 | 73 | n.s. |
| packing years | 32 ± 24 | 35 ± 23 | n.b. | n.s. |
| family history for KHE (%) | 26 | 50 | 40 | n.s. |
| KHE (1/2/3 vessel disease %) | 74/26/0 | 59/41/0 | 9/3/3 | n.s. |
| history of KHE (%) | 0 | 0 | 0 | n.s. |
| area of infarction (anterior/inferior) (%) | 65/35 | 50/50 | 60/40 | n.s. |
| infarction related vessel (%) |  |  |  |  |
| LAD | 61 | 46 | 53 | n.s. |
| LCX | 22 | 4 | 13 | n.s. |
| RCA | 17 | 5 | 34 | n.s. |
| primary therapy PTCA/stent (n) | 91 | 73 | 93 | n.s. |
| time to neovascularisation (mean value/median) | 17 ± 27/4 | 32 ± 49/14 | 16 ± 24/5 | n.s. |
| TIMI III flow post reperfusion (%) | 87 | 91 | n.d. | n.s. |
| ejection fraction (estimated visually) | 43 ± 11 | 40 ± 8 | 40 ± 7 | n.s. |
| CPR during acute MI (n) | 0 | 2 | 1 | n.s. |
| kreatinkinase max. (U/l)* | 940 ± 725 | 781 ± 630 | 915 ± 740 | n.s. |
| CK MB max. (U/l)* | 104 ± 67 | 94 ± 106 | 146 ± 128 | n.s. |
| medication after discharge |  |  |  |  |
| aspirin (%) | 100 | 100 | 93 | n.s. |
| clopidogel (%) | 100 | 100 | 100 | n.s. |
| ACE-inhibitor (%) | 96 | 100 | 93 | n.s. |
| Beta-blocker (%) | 100 | 100 | 100 | n.s. |
| statin (%) | 100 | 100 | 93 | n.s. |
| time stent to cell therapy (h) | 119 ± 27 | 111 ± 41 | — | n.s. |
| number of injected cells (Mio.) | 17 ± 12 | 219 ± 82 |  | <0.001 |
| Before cell therapy |  |  |  |  |
| number of white blood cells (/nl) | 12.4 ± 4.2 | 12.8 ± 3.6 | — | n.s. |
| C-reactive protein (mg/dl) | 2.8 ± 2.2 | 3.2 ± 2.4 | — | n.s. |
| troponin T (ng/ml) | 2.0 ± 1.4 | 2.2 ± 1.9 | — |  |
| 24 hours after cell therapy |  |  |  |  |
| number of white blood cells (/ml) | 8.5 ± 2.1 | 9.8 ± 1.9 | — | 0.02 |
| C-reactive protein (mg/dl) | 2.6 ± 2.3 | 3.1 ± 1.9 | — | n.s. |
| troponin T (ng/ml) | 1.3 ± 1.0 | 1.5 ± 1.2 | — | n.s. |

CPR = cardio-pulmonary resuscitation *without CPR-patients

TABLE 2

Quantitative global and regional LV function

|  | baseline | follow-up | p-value |
|---|---|---|---|
| BDP (n = 23) | | | |
| ejection-fraktion (%) | 49 ± 10 | 58 ± 10 | 0.004 |
| end-diastolic volume (ml) | 107 ± 25 | 108 ± 33 | n.s. |
| end-systolic volume (ml) | 53 ± 14 | 45 ± 18 | 0.035 |
| regional wall movement (SD/Chord) | | | |
| infarction | −1.5 ± 0.3 | −0.7 ± 0.6 | <0.001 |
| center of infarction | −1.6 ± 0.4 | −0.8 ± 0.7 | <0.001 |
| border of infarction | −1.5 ± 0.2 | −0.5 ± 0.6 | <0.001 |
| BMP (n = 23) | | | |
| ejection-fraktion (%) | 49 ± 10 | 59 ± 9 | 0.003 |
| end-diastolic volume (ml) | 114 ± 29 | 101 ± 33 | n.s. |
| end-systolic volume (ml) | 57 ± 21 | 43 ± 21 | 0.003 |
| regional wall movement (SD/Chord) | | | |
| infarction | −1.5 ± 0.3 | −0.5 ± 0.6 | <0.001 |
| center of infarction | −1.7 ± 0.4 | −0.7 ± 0.6 | <0.001 |
| border of infarction | −1.4 ± 0.2 | −0.4 ± 0.7 | <0.001 |
| control (n = 15) | | | |
| ejection-fraktion (%) | 50.3 ± 9.3 | 52.6 ± 9.4 | 0.379 |
| end-diastolic volume (ml) | 101.3 ± 22.6 | 120.0 ± 47.0 | 0.108 |
| end-systolic volume (ml) | 50.9 ± 16.7 | 57.6 ± 30.6 | 0.363 |
| regional wall movement (SD/Chord) | n.d. | n.d. | — |

TABLE 3

Baseline parameters between patients that received cells with a high migratory capacity compared with those receiving precursor cells with lower migratory capacity

| Baseline | high migratory capacity n = 16 | low migratory capacity n = 15 | p-value |
|---|---|---|---|
| age (years) | 48 ± 11 | 50 ± 9 | n.s. |
| gender (male/female) | 15/1 | 13/2 | n.s. |
| number risk factors (%) | 2.7 ± 0.9 | 2.6 ± 0.9 | n.s. |
| area of infarction (ant./inf; %) | 75/25 | 60/40 | n.s. |
| ejection-fraktion (%) | 48 ± 8 | 49 ± 12 | n.s. |
| end-diastolic volume (ml) | 104 ± 22 | 118 ± 25 | n.s. |
| end-systolic volume (ml) | 53 ± 15 | 59 ± 20 | n.s. |
| regional wall movement (SD/Chord) | | | n.s. |
| infarction | −1.5 ± 0.2 | −1.5 ± 0.3 | n.s. |
| infarctionmitte | −1.7 ± 0.3 | −1.6 ± 0.3 | n.s. |
| infarctiongrenze | −1.4 ± 0.2 | −1.5 ± 0.3 | n.s. |
| Partition wall movement; value | 7.0 ± 2.4 | 6.7 ± 3.0 | n.s. |
| late-amplification volume (ml) | 39 ± 44 | 35 ± 22 | n.s. |

TABLE 4A

Multivariate analysis of the independent predictive-factors of the reduction of the size of infarction

| | Δ late-amplification volume r | p-value |
|---|---|---|
| gender | −0.094 | n.s. |
| age | −0.099 | n.s. |
| time to revascularisation | 0.329 | n.s. |
| Baseline ejection fraction | 0.784 | 0.016 |
| Baseline late-amplification volume | 0.184 | n.s. |
| high/low migration | −0.883 | 0.007 |

TABLE 4B

Multivariate analysis of the independent prediction-factors of the regional improvement of the LV-function

| | Δ Partition wall movement-value r | p-value |
|---|---|---|
| gender | 0.076 | n.s. |
| age | 0.6 | 0.035 |
| time to revascularisation | 0.165 | n.s. |
| Baseline ejection fraction | 0.403 | n.s. |
| Baseline partition wall movement-value | −0.735 | 0.008 |
| high/low migration | −0.619 | 0.021 |

TABLE 5

Baseline-characteristics of the study population

| | patients with ICMP n = 18 | healthy control n = 8 | p-value |
|---|---|---|---|
| age (years) | 59.4 ± 13.4 | 54 ± 13 | <0.001 |
| Male gender (%) | 88.9 | 87.5 | 0.65 |
| hypertension (%) | 57 | 0 | <0.001 |
| hyperlipidaemia (%) | 70 | 25 | <0.001 |
| diabetes (%) | 17 | 0 | <0.001 |
| smoker (%) | 82.4 | 37.5 | <0.001 |
| Family history of KHE (%) | 52.9 | 25.0 | <0.001 |
| KHE (1/2/3 vessel disease %) | 17.6/52.9/29.4 | n.a. | |
| History of KHE (%) | 100 | n.a. | |
| Area of infarction (anterior/inferior) (%) | 65/35 | n.a. | |
| Ejection fraction (estimated visually) | 37.8 ± 11.1 | 62.6 ± 3.1 | <0.001 |
| medication after discharge | | | |
| aspirin (%) | 100 | 0 | |
| clopidogel (%) | 100 | 0 | |
| ACE-inhibitor (%) | 100 | 0 | |
| betablocker (%) | 100 | 0 | |
| statin (%) | 100 | 0 | |
| C-reactive protein (mg/dl) | 3.0 ± 2.5 | 2.9 ± 1.7 | 0.51 |
| number of white blood cells (×10$^3$/nl) | 7.9 ± 3.7 | 6.8 ± 2.9 | 0.85 |

TABLE 6

Univariate linear regression analysis of the relationships between clinical characteristics as well as the measurements in vitro and the neovascularisation-capacity of BMPs in a mouse model of rear-limb ischemia

| | patients and healthy controls | | patients only | |
|---|---|---|---|---|
| | r | p-value | r | p-value |
| age | −0.38 | 0.064 | 0.260 | 0.33 |
| gender | 0.032 | 0.87 | −0.165 | 0.49 |
| hypertension | −0.646 | 0.001 | −0.204 | 0.43 |
| hyperlipidaemia | −0.598 | 0.002 | 0.114 | 0.68 |
| Family history of KHE | −0.403 | 0.019 | 0.134 | 0.61 |
| diabetes | −0.641 | 0.001 | −0.088 | 0.74 |
| number of risk factors | −0.540 | 0.006 | 0.174 | 0.52 |
| NYHA classification | −0.630 | 0.001 | −0.116 | 0.66 |
| ejection fraction (%) | 0.720 | 0.001 | 0.315 | 0.273 |
| basal migration | 0.380 | 0.061 | 0.456 | 0.05 |
| SDF-1 induced migration | 0.781 | <0.001 | 0.634 | 0.004 |
| VEGF induced migration | 0.352 | 0.078 | 0.374 | 0.13 |
| Colony-forming capacity | 0.740 | <0.001 | 0.074 | 0.785 |

The invention claimed is:

1. A method for stratifying mammalian subjects having at least one cardiovascular disease, comprising:
   a) isolating, from a biological sample obtained from a mammalian subject having at least one cardiovascular disease, bone marrow-precursor-cells (BMP) and/or blood-derived circulating precursor-cells (BDP) by means of at least one cell specific surface marker;
   b) performing a cell migration assay on the BMP and/or BDP to provide an assessment of migratory capacity thereof;
   c) determining, based on the assessed migratory capacity, the cardiovascular functionality of BMP and/or BDP; and
   d) determining, based on the determined cardiovascular functionality, whether the subject would benefit from cell therapy and/or an ex vivo pretreatment of their BMPs or BDPs before retransplantation of the cells to provide for improvement of subject's cardiovascular functionality, wherein a method for stratifying mammalian subjects having at least one cardiovascular disease is afforded.

2. The method according to claim 1, further comprising the comparison of the assessed migratory capacity and/or the determined cardiovascular functionality result as obtained from the sample as examined with a reference value and/or the result of a reference sample.

3. The method according to claim 1, wherein the sample to be examined is derived from a human.

4. The method according to claim 1, wherein the sample to be examined is selected from the group consisting of bone marrow, peripheral blood or fractions thereof and cell culture-suspensions or fractions thereof.

5. The method according to claim 4, wherein a coagulation inhibitor is added to the peripheral blood.

6. The method according to claim 4, wherein the sample to be examined is obtained by means of punctuation from the bone marrow.

7. The method according to claim 1, wherein the isolating occurs by using density-gradient-centrifugation, cell specific surface markers, and/or immunological methods.

8. The method according to claim 7, wherein the isolating occurs by using FACS or immunomagnetic separation.

9. The method according to claim 1, wherein the cell specific surface marker for BMP is selected from CD34, CD45 and CD133, and for BDP is selected from VEGFR2, CD105, vWF and CD31.

10. The method according to claim 1, wherein the migration assay is performed in a Boyden-chamber or a modified Boyden-chamber.

11. The method according to claim 1, wherein the migration assay is performed using SDF-1, VEGF, P1GF or MCP-1.

12. The method according to claim 1, wherein the cardiovascular disease is selected from the group consisting of stable and unstable angina, stable coronary heart disease, acute coronary syndrome, myocardial infarction, acute myocardial infarction, acute heart syndrome, coronary artery disease, chronic ischemic cardiomyopathy (ICMP), dilatative cardiomyopathy (DCM), heart insufficiency, and other causes of a cardiac weakness.

13. The method according to claim 1, wherein the method is performed immediately before a cell infusion into the mammal.

14. The method according to claim 1, wherein the examined isolated BMP and/or BDP are autologous and/or heterologous for the mammal.

15. The method of claim 1, comprising placement of the subject into a stratified classification group.

16. The method of claim 1, further comprising administration of cell therapy to the stratified subject.

17. The method of claim 16, wherein cell therapy comprises administration of at least one of bone marrow-precursor-cells (BMP) and blood-derived circulating precursor-cells (BDP).

18. The method of claim 17, wherein administration comprises infusion of cells into the subject.

19. The method of claim 17, comprises administration of at least one of a statin, VEGF, and erythropoietin.

20. The method of claim 19, wherein the statin comprises atorvastatin.

* * * * *